(12) United States Patent
Fattinger et al.

(10) Patent No.: US 9,201,084 B2
(45) Date of Patent: Dec. 1, 2015

(54) SYSTEM AND METHOD FOR ROBOTIC STORAGE OF MICROPLATES

(75) Inventors: Christof Fattinger, Blauen (CH); Remo Anton Hochstrasser, Oberwil (CH); Dieter Voegelin, Sissach (CH); Thomas Zumstein, Therwil (CH)

(73) Assignee: F. HOFFMAN-LA ROCHE AG, Basel (CH)

( * ) Notice: Subject to any disclaimer, the term of this patent is extended or adjusted under 35 U.S.C. 154(b) by 1532 days.

(21) Appl. No.: 12/587,085

(22) Filed: Sep. 30, 2009

(65) Prior Publication Data
US 2010/0086440 A1     Apr. 8, 2010

(30) Foreign Application Priority Data

Sep. 30, 2008    (EP) .................................. 08165472

(51) Int. Cl.
*G01N 35/10* (2006.01)
*G01N 35/02* (2006.01)
*G01N 35/00* (2006.01)
*G01N 35/04* (2006.01)

(52) U.S. Cl.
CPC .......... *G01N 35/028* (2013.01); *G01N 35/0099* (2013.01); *G01N 2035/00435* (2013.01); *G01N 2035/0425* (2013.01)

(58) Field of Classification Search
CPC .................. G01N 2035/00435; G01N 35/0099
USPC ............. 422/500, 297, 300, 565, 63, 67, 167; 414/331.05, 416.04, 416.09; 221/41.12, 163, 277, 268, 62, 224
See application file for complete search history.

(56) References Cited

U.S. PATENT DOCUMENTS

| | | | | |
|---|---|---|---|---|
| 5,325,967 | A * | 7/1994 | Gonzales | 206/462 |
| 6,536,859 | B1 * | 3/2003 | Bathe | 312/305 |
| 2002/0012611 | A1 * | 1/2002 | Stylli et al. | 422/65 |
| 2003/0009251 | A1 * | 1/2003 | Lin et al. | 700/97 |
| 2003/0215357 | A1 * | 11/2003 | Malterer et al. | 422/50 |
| 2006/0039781 | A1 * | 2/2006 | Niewmierzycki et al. | 414/217 |

OTHER PUBLICATIONS

Publication of REMP AG (Sample Storage Systems, REMP Storage Family, Jan. 2007 (6 pgs.).
Publication of REMP AG (Remp Installations, First −80° C. BioBank, Jan. 2007 (2 pgs.).

* cited by examiner

*Primary Examiner* — Natalia Levkovich
(74) *Attorney, Agent, or Firm* — Mintz Levin Cohn Ferris Glovsky and Popeo, P.C.

(57) ABSTRACT

A robotic microplate storage system includes a freezer room having freezing units and a first robot for moving and removing microplates into and out of the freezing unit. The first robot can also transfer microplates to a processing station, where the microplates are stored in a microplate recipient within the freezing unit. The storage system may also include at least one processing room which is thermally separated from the freezer room. Each processing room may include a processing station having a tube transfer module and a second robot for moving the microplates between the microplate recipients and the tube transfer module. The first robot may be designed such that it is only capable of removing a microplate recipient from and moving it into a freezing unit as well as transferring it from a freezing unit to a processing station or vice versa.

15 Claims, 10 Drawing Sheets

SYSTEM AND METHOD FOR ROBOTIC STORAGE OF MICROPLATES

RELATED APPLICATIONS

The present application claims benefit and priority to European patent application no. 08165472.5, filed 30 Sep. 2008, the entire disclosure of which is herein incorporated by reference.

BACKGROUND OF THE DISCLOSURE

Embodiments of the present invention relate to a robotic storage system for storing microplates carrying a plurality of sample tubes. More particular, in some embodiments, the robotic storage system comprises a freezer room having a plurality of freezing units and a first robot being capable of removing a microplate from and moving a microplate into a said freezing unit. The robot may be further capable of transferring the microplate to a processing station. The present disclosure also relates to a stacker adapter for use in a robotic storage system and a container, in some embodiments, a cardboard box, for shipping a stack of microplates used in a robotic storage system.

In clinical studies a wide variety of assays can be carried out to answer questions related to diagnosis (e.g. biomarker), treatment (e.g. efficacy of a drug) and prevention of diseases.

Large sample collections of biological samples can be established e.g. within the context of clinical studies. Such biological samples can be e.g. blood samples (whole blood, plasma, serum), urine samples, tissue samples, or samples containing cells (e.g. primary cells, stem cells), proteins, DNA, RNA (RNAi, mRNA), or antibodies. The samples are frequently used in small amounts, for example in the range of few microliters, and handled in sample tubes which are removably arranged in microplates. Such sample tubes can be advantageous since they can be sealed and thereby easily transferred between several microplates in a sealed state. Particularly, when the samples additionally are held frozen inside the sample tubes, they can efficiently be transferred from one microplate to another microplate without impairing the frozen state of the samples.

Such biological samples are typically stored at a temperature of about $-80°$ C. in specific humidity controlled rooms. Cooling of a complete humidity controlled room for storing biological samples as described above to about $-80°$ C. (or below) is generally feasible. However, at said temperatures standard handling devices, such as for example robots, usually do not work properly. Therefore, particularly for long-term storage of biological samples, specific $-80°$ C. freezers are typically used.

Such freezers for long term storage of samples usually have a tight and thermally insulating door which separates the environment outside the freezer from the $-80°$ C. interior of the freezer. In a robotic storage system, a plurality of such freezers is arranged in a $-20°$ C. room as well as a robot for taking the samples out of the respective freezer. As mentioned above, the robot cannot be arranged in a $-80°$ C. environment, since this simply is not economically feasible in such an environment, and in addition maintenance of the robot would be difficult then. Instead, the robot is arranged outside the freezers in the $-20°$ C. environment where it is capable of working properly.

A robotic storage system belonging to the state of the art, e.g. Bio-Sample Store™ from REMP AG, Switzerland, comprises freezers having a temperature of about $-80°$ C. and a freezer room having a temperature of about $-20°$ C. The freezers are aligned on each side of a corridor of the freezer room and a robot is movable along the corridor on tracks installed on the floor in the corridor. Whenever a specific sample tube is requested, the robot opens the corresponding freezer and removes the microplate carrying the specific sample tube from a drawer of the freezer. Then, the robot removes the sample tube from this source microplate and transfers it to a destination microplate which is arranged beneath the source microplate. This step is performed by transferring the sample tube through the source microplate into the destination microplate. After tube transfer has been performed, the robot moves the source microplate back into the drawer of the freezer. Once the destination microplate has been filled with all desired sample tubes, the robot moves the destination microplate to a hand-over point.

However, this known robotic storage system has a number of disadvantages. Firstly, the temperature difference of about $60°$ C. between the temperature in the freezer room ($-20°$ C.) and the temperature in the freezers ($-80°$ C.) results in the creation of considerable amounts of ice inside the freezers and on the microplates whenever humidity enters the freezer upon accessing a microplate.

Secondly, as the robot has to fulfill all the afore-mentioned tasks (opening a freezer, removing a microplate from a drawer of the freezer, tube transfer into a destination microplate, moving the microplate back into the drawer of the freezer, further tube transfer of other sample tubes into the same destination microplate, moving of the destination microplate to a hand-over point) one after the other, it is of a very complex construction and is therefore very expensive. On the other hand, the various functions of the robot are not efficiently used.

Thirdly, as the robot is permanently arranged in the freezer room at about $-20°$ C., maintenance work has to be performed under difficult conditions. Given these conditions, security provisions of several countries require a minimum of two workers to enter the freezer room together at the same time for performing the maintenance work.

SUMMARY OF THE EMBODIMENTS

Therefore, it is an object of some of the embodiments of the disclosure to provide a robotic storage system either which substantially reduces or which does not even have the afore-described disadvantages.

This object may be achieved by the robotic storage according to some embodiments, as it is characterised by the features of one or another of the independent claims. Advantageous embodiments of the robotic storage system according to the disclosure become apparent from the features of the dependent claims.

In particular, the robotic storage system according to some embodiments for storing microplates carrying a plurality of sample tubes comprises a freezer room having a plurality of freezing units and a first robot being capable of removing a microplate from and moving a microplate into a said freezing unit. The first robot is further capable of transferring the microplate to a processing station. The microplates are stored in the freezing units such that a plurality of microplates are arranged one above the other in a microplate receiving section (a microplate receiving section may also be referred to as a "microplate recipient"). The robotic storage system comprises at least one processing room and means for thermally separating the processing room from the freezer room. Each processing room comprises a processing station having at least one tube transfer module, and optionally at least one temporary hotel, as well as a second robot for moving the microplates between the microplate recipients, said at least one tube transfer module and said optionally at least one temporary hotel. The first robot is designed such that it is only capable of removing a said microplate recipient from and moving it into a said freezing unit as well as of transferring it from a said freezing unit to a processing station or vice versa.

The use of microplate recipients in which a plurality of microplates are stored one above the other, in some embodiments, substantially reduces the formation of ice on the microplates due to the tightly stacked arrangement of the microplates.

The means for thermally separating the at least one processing room from the freezer room enable maintenance of the first robot (when moved into the processing room), of the processing station and of the second robot under more convenient conditions, while the freezer room is kept at about −20° C. For example, the processing room can be "heated" to a temperature in the range of +4° C. to +10° C., so that it is possible to have only a single person perform the maintenance work.

The first and the second robot, in some embodiments, each have only a few well-defined tasks to fulfill, which are assigned to these first and second robots, respectively, in a manner such that the robotic storage system can be operated with high efficiency. In particular, since the first robot is designed such that it is only capable of removing microplate recipients from and for moving microplate recipients into the freezing unit, the first robot can be of a simple construction and requires less maintenance. The first and second robots can perform their tasks independently from one another in a highly efficient manner, thus providing a high performance of the entire robotic storage system.

In another embodiment of the robotic storage system according to the invention, the robotic storage system comprises a freezer room and first and second processing rooms. The first and second processing rooms are arranged at opposite ends of the freezer room. The first robot is capable of transferring microplate recipients to either one of the first and second processing rooms. Provision of two processing rooms allows to continue operation of the robotic storage system while in one of the two processing rooms maintenance work is done. The arrangement of the two processing rooms at opposite ends of the freezer room only requires a simple straight track for the first robot, this straight track connecting the freezer room to both processing rooms.

In a further embodiment of the robotic storage system according to the invention, the freezer units comprise freezers. Each freezer comprises a door and a plurality of drawers inside the freezer, with each drawer being designed to store a plurality of microplate recipients. Inside the freezers the temperature is about −80° C., whereas the temperature inside the freezer room is about −20° C. Freezers with doors enable thermal insulation of the −80° C. environment inside the freezers from the −20° C. environment in the freezer room. Since normally only one drawer is opened at a time, only little humidity can flow into the freezer and less "heating" occurs inside the freezer whenever the door is open.

In yet a further embodiment of the robotic storage system according to the invention, the means for thermally separating the respective processing room from the freezer room comprise a thermally insulating door. The thermally insulating door is simple from a constructional point of view and allows to easily separate the respective processing room from the freezer room. As an example, the thermally insulating door can be a foldable door.

In still a further embodiment of the robotic storage system according to the invention, the first robot comprises means for carrying at least two microplate recipients at a time. Therefore, the first robot can move one microplate recipient from the processing station to a freezer, remove a microplate recipient that has to be brought to the processing station from the drawer and place the microplate recipient transferred from the processing station in the thus resulting space. This embodiment further improves the efficiency of the robotic storage system according to the invention.

In yet another embodiment of the robotic storage system according to the invention, the microplate recipients comprise stackers and/or storage hotels. Stackers and storage hotels are essentially rectangular microplate recipients storing microplates arranged one above the other. The stacker has closed side walls and a closed top wall leaving only a bottom opening open, whereas the storage hotel has at least one side (typically the front side) open for allowing access of each microplate. Retaining rails are provided for each microplate inside the storage hotel and small gaps are required between the various microplates arranged in a storage hotel for allowing access by the second robot.

With regard to the stacker, according to some embodiments, a stack of microplates with essentially no gaps between the microplates is stored in the stacker. Thus, the stacker has a higher "packing density" compared to a storage hotel of the same size. As the stack of microplates essentially has no gaps between the microplates thermal insulation for the stacker is also improved when compared to a storage hotel.

In another embodiment of the robotic storage system according to the invention, the processing station further comprises at least one docking unit for receiving microplate recipients transferred by the first robot to the processing station and for allowing the first robot to transfer microplate recipients from the processing station to the freezing units. The docking units on the processing stations act as an interface between the first and the second robot. The first robot moves microplate recipients from the freezer room to the processing room and places them into a said docking unit of the processing station. The second robot is then in charge for moving the microplates of the microplate recipient either into a tube transfer module, optionally a temporary hotel for temporary storage or in another microplate recipient getting ready to be transferred by the first robot. The said tube transfer module can be a tube punching module or a tube picking module. If at least one of the microplate recipients is a stacker, the processing station comprises preferably a temporary hotel for temporary storage.

In a further embodiment of the robotic storage system according to the invention, the docking units for microplate recipients comprise means for allowing access to each of the microplates arranged in a said stacker and/or in a said storage hotel. Access to each of the microplates reduces the overall time required to perform the required operations in the processing station, especially if the uppermost microplate of a stack of a stacker has to be accessed.

In another further embodiment of the robotic storage system according to the invention, the means for allowing access to each of the microplates arranged in a said stacker comprise releasing means for actuating a retaining means of the stacker, thus allowing release of the stack of the microplates from the stacker. In addition, these means comprise a lift for lowering the released stack of microplates to the desired microplate. The stacker comprises a stack of microplates that has been inserted into the stacker through the bottom opening of the stacker. Retaining means are provided to retain the stack of microplates inside the stacker. The retaining means have to be released for loading and unloading of the stacker with microplates. A stacker only allows removing of the lowermost microplate at a time. The use of a lift enables, however, to lower of an entire stack of microplates to the desired microplate and to remove the desired microplate from the stack of microplates, without having to unload the microplates one by one until the desired microplate is the lowermost microplate. This embodiment further improves the efficiency of the robotic storage system according to the invention.

In yet another embodiment of the robotic storage system according to the invention, the storage hotels comprise a cover. The means for allowing access to each of the microplates arranged in a said storage hotel comprise means for removing the cover. Microplates arranged in a storage hotel generally are less thermally insulated compared to those arranged in a stacker due to the required gaps between the microplates and due to the at least one side being open for accessing the microplates. The cover provides additional thermal insulation to the microplates arranged in the storage hotel. In order to allow access to each of the microplates arranged in the hotel, the cover has to be removed.

In yet a further embodiment of the robotic storage system according to the invention, the respective processing room comprises an intermediate freezer for intermediate storage of microplate recipients which have been customised in the processing station in accordance with a user's request. The intermediate freezer is accessible from inside the processing room by the first robot for moving microplate recipients into the intermediate freezer or for removing microplate recipients from the intermediate freezer, and from outside the processing room by the user for removing microplate recipients from the intermediate freezer or moving microplate recipients into the intermediate freezer. The intermediate freezer works as a gateway between the user and the robotic storage system. In the processing station microplate recipients are assembled carrying desired microplates in accordance with a user's request. Such "customised" microplate recipients are then moved by the first robot to the intermediate freezer, where they can be store until the user requests them at the gateway window. The inside of the intermediate freezer may also be kept at about −80° C. Therefore, a stay in the intermediate freezer is of no harm to the samples.

A further aspect of the invention relates to a stacker adapter for use in the above-described robotic storage system. The stacker adapter comprises means for matching microplate stackers, which are incompatible with the docking units of the processing station. The stacker adapter comprises first engagement means for receiving incompatible stackers and second engagement means for allowing the stacker adapter to be received by the respective docking unit. The stacker adapter further comprises first means for actuating the retaining means of the stacker whenever the stacker is inserted in the stacker adapter. The stacker adapter further comprises second means for retaining the released stack of microplates in the stacker whenever they are not actuated by the releasing means of the docking unit, and for releasing the said stack of microplates from the stacker upon actuation by the said releasing means. Such a stacker adapter enables the use of stackers as made by different manufacturers to be used with one and the same processing station.

According to another further aspect of the invention, a container, and in some embodiments, such a container may be a cardboard box, for shipping a stack of microplates used in the above-described robotic storage system comprises means for securing the microplates arranged one above the other in the cardboard box. Such a cardboard box permits cost-effective shipping of microplates, thus eliminating the risk of losing a stacker or storage hotel that is not returned afterwards, since a stacker or storage hotel is no longer needed. Several cardboard boxes can be placed together in a larger container before shipping, and the larger container can be further sealed with a plastic foil.

In a further embodiment of the cardboard box/container according to the invention, the cardboard box has a rectangular horizontal cross-section, and the means for securing the microplates comprise deformable sections diagonally oppositely arranged on at least two edges of the cardboard box. Deformable pre-perforated sections enable safe securing of the microplates stored inside the cardboard box. Several deformable pre-perforated sections are provided at well-defined distances corresponding to the size of the microplates. Depending on the number of microplates inserted into the cardboard box, different deformable sections have to be activated.

BRIEF DESCRIPTION OF THE DRAWINGS

Further advantageous aspects of the robotic storage system according to the invention become evident from the following detailed description of the specific embodiments with the aid of the drawings, in which.

DETAILED DESCRIPTION OF THE EMBODIMENTS

Figure 1:
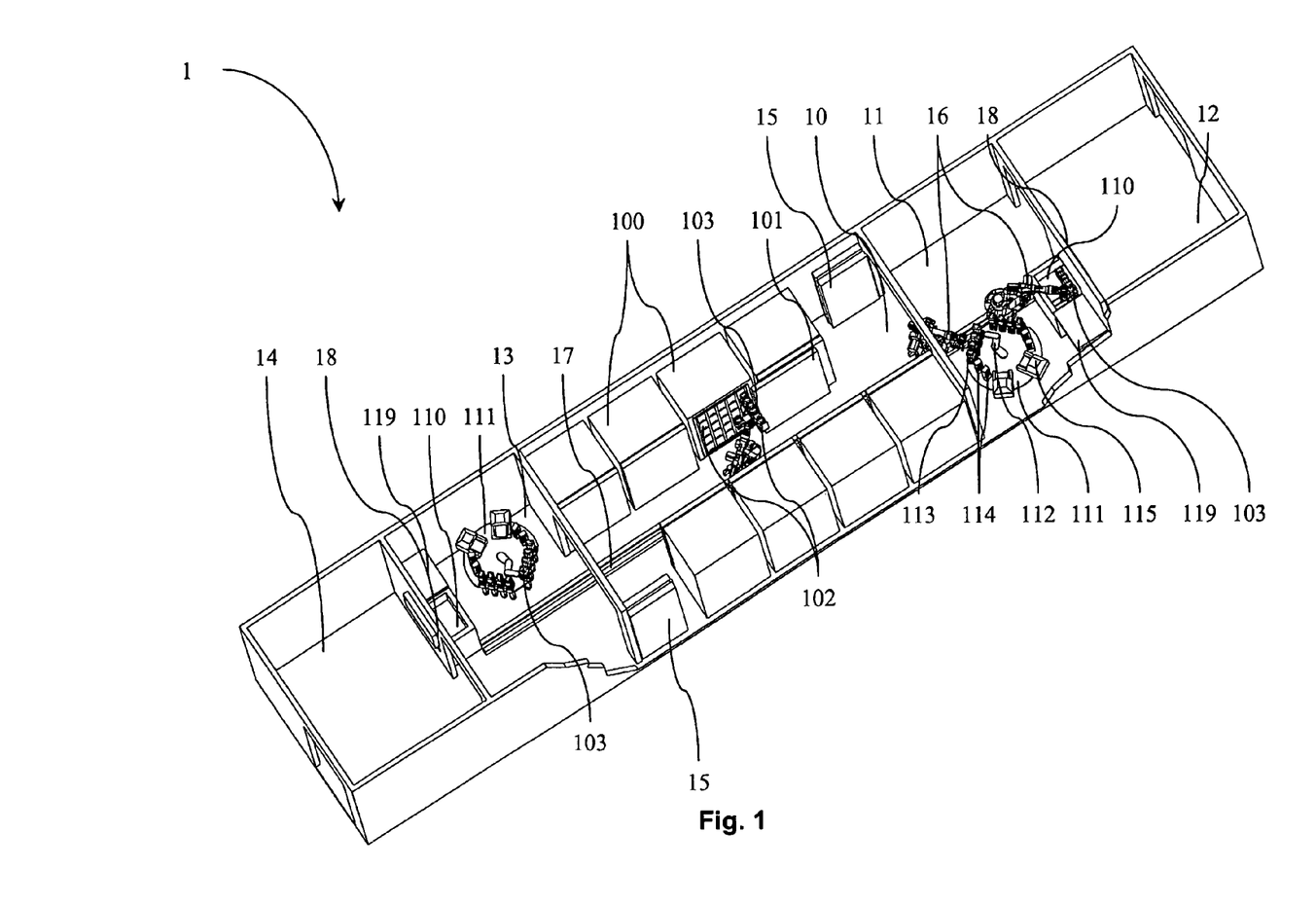
FIG. 1 shows a perspective view of an embodiment of a robotic storage system according to some embodiments.
Figure 2:
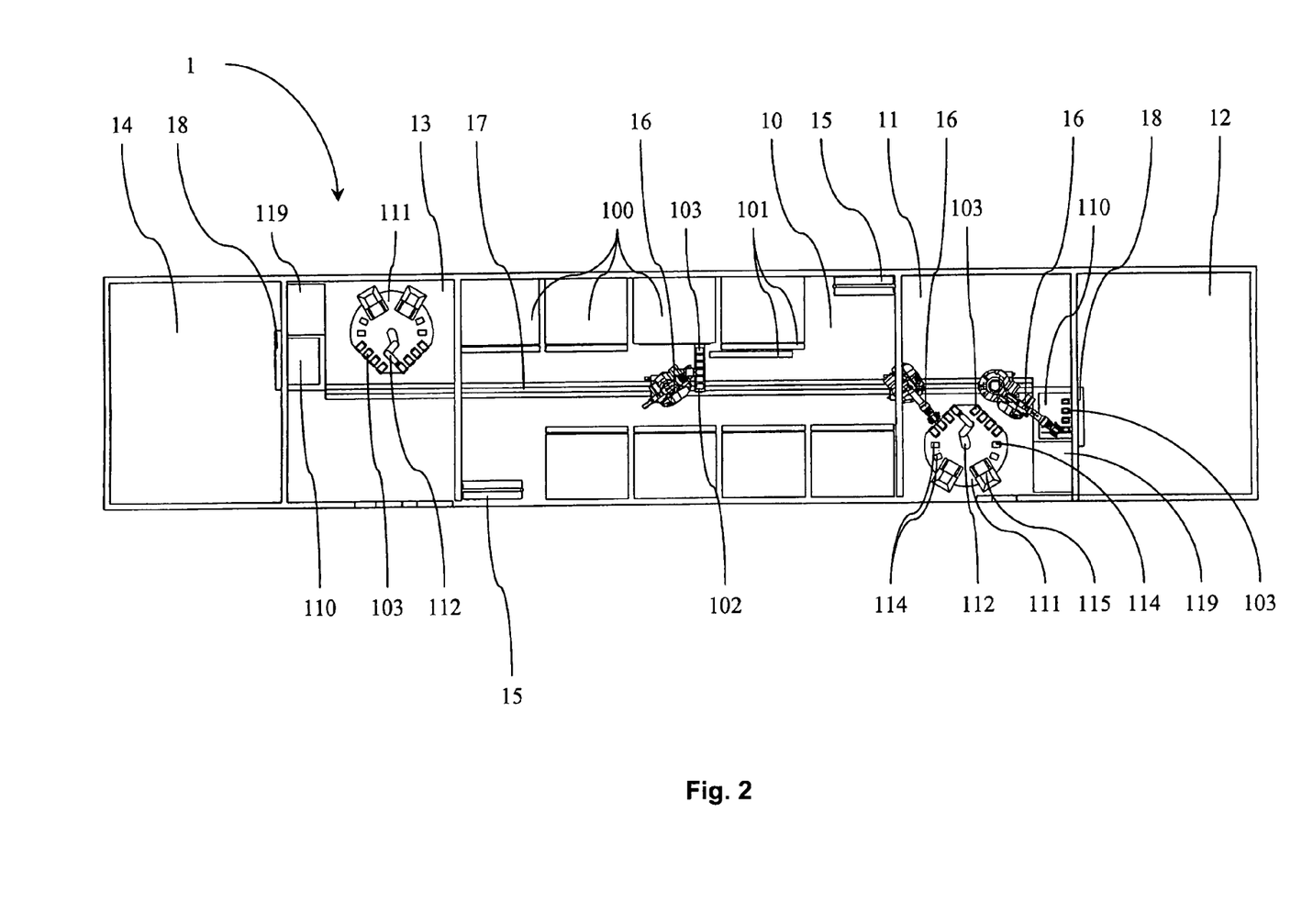
FIG. 2 shows a top view of the robotic storage system of FIG. 1.

FIGS. 1 and 2 show a perspective view and a top view of an embodiment of a robotic storage system 1 according to the invention. The robotic storage system 1 comprises a freezer room 10 and first 11 and second 13 processing rooms. The first 11 and second 13 processing rooms are arranged at opposite ends of the freezer room 10. A first handling room 12 is arranged adjacent to the first processing room 11 and a second handling room 14 is arranged adjacent to the second processing room 13. Slidably arranged foldable thermally insulating doors 15 are arranged at opposite ends of the freezer room 10 for thermally separating the first 11 and second 13 processing rooms from the freezer room 10. The temperature of the freezer room 10 may, for example, be about −20° C., whereas the temperature of the first 12 and second 14 handling rooms may, for example, be in the range of +4° C. to +10° C. The temperature of the first 11 and second 13 processing rooms during operation is essentially the same as for the freezer room 10, i.e. about −20° C. After closing of the respective foldable door 15 it is, however, possible to "heat" the corresponding first 11 or second 13 processing rooms to the same temperature as the adjacent first 12 or second 14 handling room, i.e. to a temperature in the range of +4° C. to +10° C. This is especially advantageous in case maintenance operations have to be performed inside the first 11 or second 13 processing room. With such temperatures, it is allowed that single operators enter the first 11 or second 13 processing rooms for performing the maintenance jobs, and at the same time maintenance jobs can be performed in a more convenient environment.

The freezer room 10 comprises a plurality of freezers 100. Each freezer 100 comprises a front door 101 and a plurality of drawers 102 inside the respective freezer 100. Each drawer 102 may include a plurality of microplate receiving sections 103 for receiving and storing a plurality of microplates. Microplate receiving section may also be referred to as a microplate recipient.

The robotic storage system 1 comprises a first robot 16 running on a track 17 installed on the floor and connecting the freezer room 10 to the first 11 and second 13 processing rooms. It is also possible to have more than one first robot 16 running on the same track 17 in order to increase performance of the robotic storage system 1.

The first 11 and second 13 processing rooms each comprise a processing station 111. The processing station 111 has temporary hotels 114 for temporary storage of microplates, tube transfer modules 115, and docking units 113 (best seen in FIGS. 3 and 4) for receiving microplate recipients 103 transferred by the first robot 16 from the freezers 100 to the processing station 111. The docking units 113 also allow the first robot 16 to transfer microplate recipients 103 from the processing station to the freezers 100. The processing station 111 further comprises a second robot 112 for moving microplates between microplate recipients 103 which are inserted in the docking units 113, the temporary hotels 114 and the tube transfer modules 115. The processing station 111 can be for example of the type BioCel® Automation System from the company Velocity11 Automation Solutions, Santa Clara, Calif., USA.

The temporary hotels 114 comprise a rack with three side walls, a bottom wall and a top wall. The front of the temporary hotels 114 is open. Retaining rails are provided for the temporary storage of microplates on different levels in the respective temporary hotel 114.

The first 11 and second 13 processing rooms each comprise an intermediate freezer 110 for intermediate storage of microplate recipients 103 which have been customised—that is to say they are in accordance with a selection of microplates or individual sample tubes specified by a user—in the processing station 111 of the first 11 or second 13 processing room.

The intermediate freezer 110 is accessible from inside the respective processing room 11, 13 by the first robot 16, for moving microplate recipients 103 into the intermediate freezer 110 or for removing microplate recipients 103 from the intermediate freezer 110, and for providing access to microplate recipients 103 from outside the respective processing room 11, 13 to the user for removing customised microplate recipients 103 or for returning microplate recipients 103 into the intermediate freezer 110. The user accesses the customised microplate recipients 103 through a window 18 connecting the first 12 or second 14 handling room with the corresponding first 11 or second 13 processing room. By way of example, the temperature inside the intermediate freezer is about −80° C. (similar to that in the freezers 100) and the intermediate freezer 110 comprises a lid 119 for thermally insulating the inner space of the intermediate freezer 110 from the respective processing room 11, 13 the temperature of which is about −20° C.

Whenever microplate recipients 103 are to be stored in the robotic storage system, the microplate recipients 103 are moved by the user into the respective processing room 11, 13 through the window 18.

For providing a desired microplate of a microplate recipient 103 or a desired sample tube of a specific microplate the first robot 16—after having taken out the respective microplate recipient 103 from the respective freezer 100—moves the microplate recipient 103 from the respective freezer to a docking unit 113 of a processing station 111. In case all sample tubes of a microplate are desired, the second robot 112 removes the desired microplate (source microplate) from the microplate recipient 103 and puts it in a destination microplate recipient 103 being filled only with desired microplates. If carrying only one or more (but not all) desired sample tubes, the second robot 112 moves the source microplate into a tube transfer module 115. The desired sample tubes are then transferred by transfer the desired tubes from the source microplate into a destination microplate. The destination microplate is finally moved to the destination microplate recipient 103 which is filled with microplates carrying only desired sample tubes. The final destination microplate recipient 103 carrying only desired sample tubes is transferred by the first robot 16 into the intermediate freezer 110.

Figure 3:
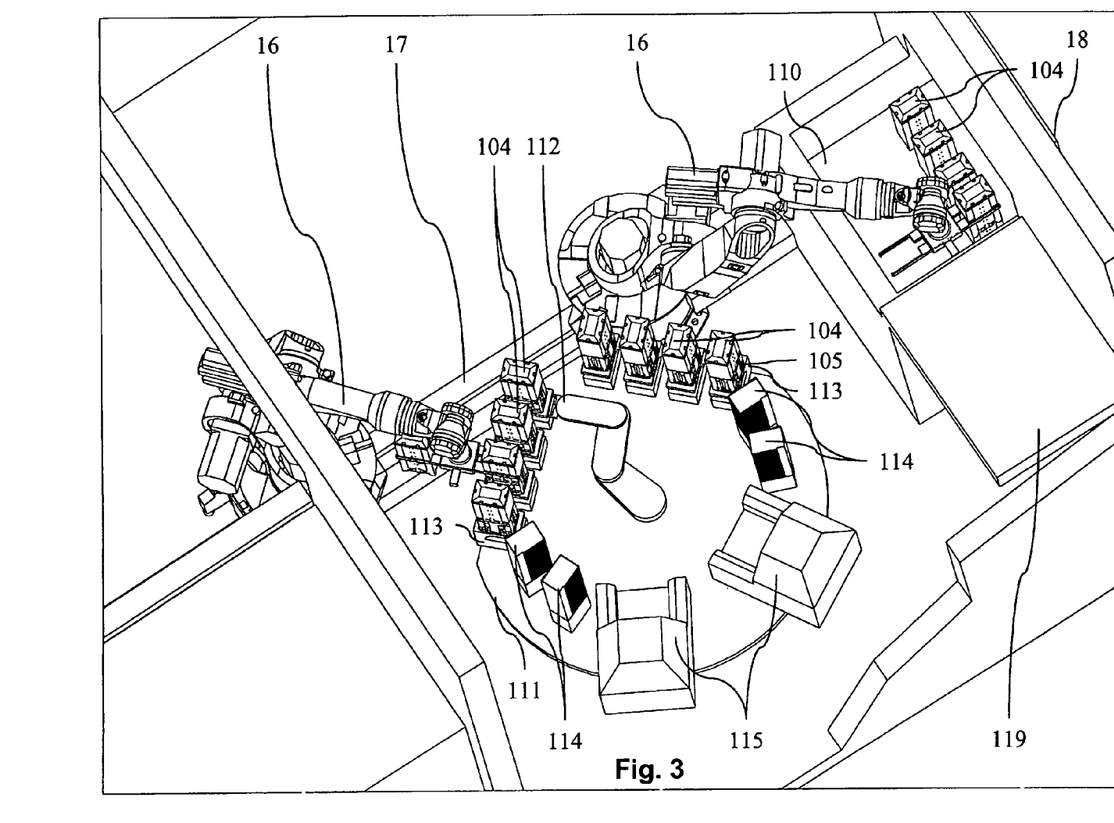
FIG. 3 shows in detail a processing station of the robotic storage system of FIG. 1, according to some embodiments, with stackers as microplate recipients being shown in the processing station.

FIG. 3 shows in detail a processing station 111 of the first or the second processing room of the robotic storage system, wherein stackers 104 fully inserted into stacker adapters 105 are shown with the stacker adapters 105 being inserted in docking units 113 of the processing station 111. The processing station 111 further comprises temporary hotels 114, tube transfer modules 115 and a second robot 112 for moving microplates between stackers 104 (inserted via the corresponding stacker adapters 105 in the docking units 113), the temporary hotels 114 and the tube transfer modules 115. A plurality of microplates 107 (see FIG. 6) is stored one above the other in a said stacker 104. The docking units 113 comprise means for allowing access to each of the microplates arranged in the stacker 104. These means for allowing access to the microplates comprise releasing means (not shown) for actuating resilient clamps 1042 (see FIGS. 6 and 7) serving as means for retaining the microplates within the stacker. By pulling apart the resilient clamps 1042 the stack of the microplates contained in a stacker 104 is released, and a lift 1130 (see FIG. 13) allows to lower the released stack of microplates to the desired microplate. The second robot 112 can only access one microplate of the stacker 104 at a time and, therefore, the lift of the docking unit allows lowering of the released stack to the desired microplate, so that the second robot 112 can access the desired microplate and it is not necessary, therefore, to individually sequentially remove one microplate after the other to arrive at the desired microplate.

Figure 4:
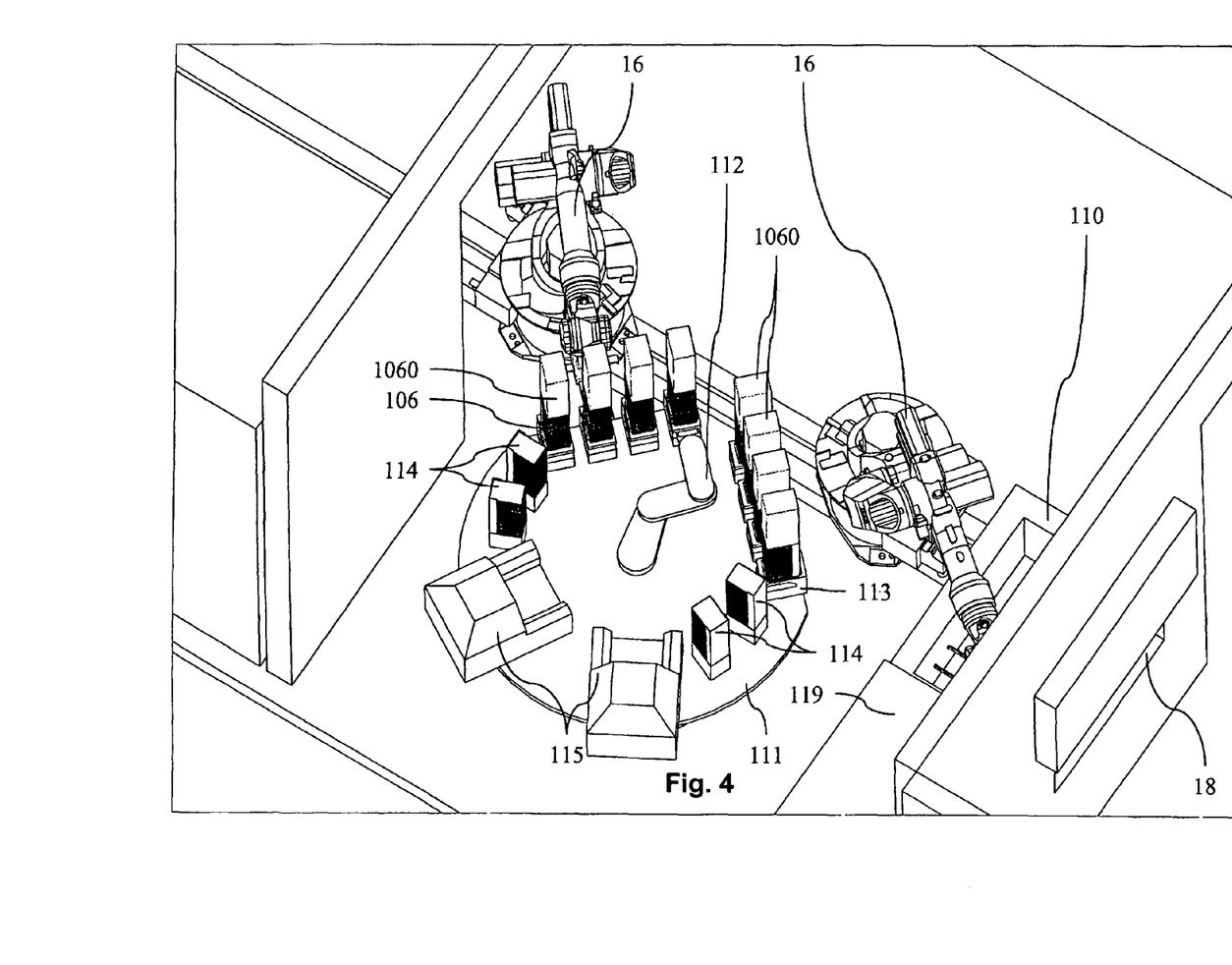
FIG. 4 shows in detail a processing station of the robotic storage system of FIG. 1, with storage hotels as microplate recipients being shown in the processing station, according to some embodiments.

FIG. 4 shows in detail a processing station 111 of the first or the second processing room of the robotic storage system, wherein storage hotels 106 as microplate recipients inserted into docking units 113 on the processing station 111 are shown. The processing station 111 further comprises temporary hotels 114, tube transfer modules 115 and a second robot 112 for moving microplates between storage hotels 106, the temporary hotels 114 and the tube transfer modules 115. The storage hotels 106 are similar to the temporary hotels 114 but in addition comprise a cover 1060. The docking units 113 comprise means for allowing access to each of the microplates arranged in a said storage hotel 106. These means for allowing access to each of the microplates arranged in a said storage hotel 106 comprise means for removing the cover 1060. In the embodiment shown, these means are designed such that they are capable of lifting the cover 1060 from the rest (i.e. the rack) of the storage hotel 106. The second robot 112 can directly access all microplates stored in the storage hotel 106, but due to its design it can only remove and transport one microplate at a time.

Figure 5:
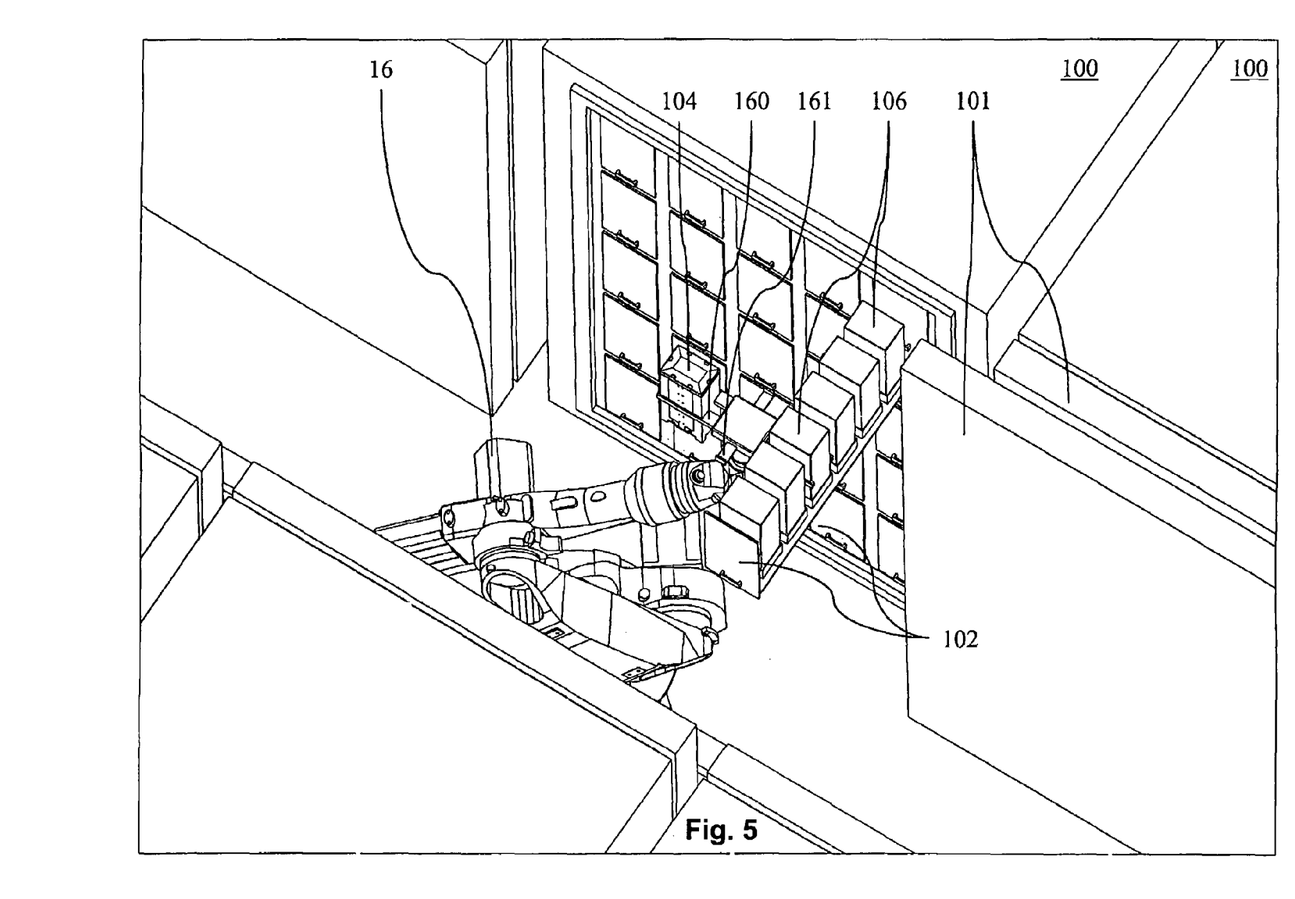
FIG. 5 shows a first robot accessing a storage hotel of a freezer of the robotic storage system of FIG. 1, according to some embodiments.

FIG. 5 shows the first robot 16 accessing a storage hotel 106 stored in a freezer 100, while carrying a stacker 104 at the same time. The first robot 16 comprises means 160 for carrying two microplate recipients, i.e. stackers 104 and/or storage hotels 106, at the same time as well as means 161 for opening and closing a drawer 102 of a freezer 100. Therefore, the first robot 16 can move one microplate recipient from the processing station to a freezer 100, remove from a drawer 102 a microplate recipient that has to be brought to the processing station, and insert into the thus created space the microplate recipient being returned from the processing station.

Figure 6:
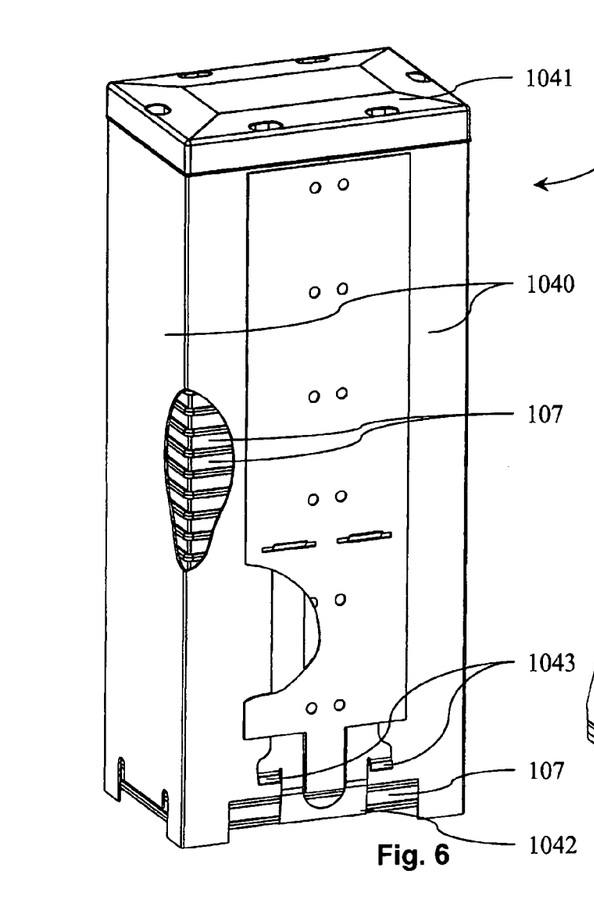
FIG. 6 shows a perspective view of an embodiment of a stacker for use in the robotic storage system of FIG. 1.
Figure 7:
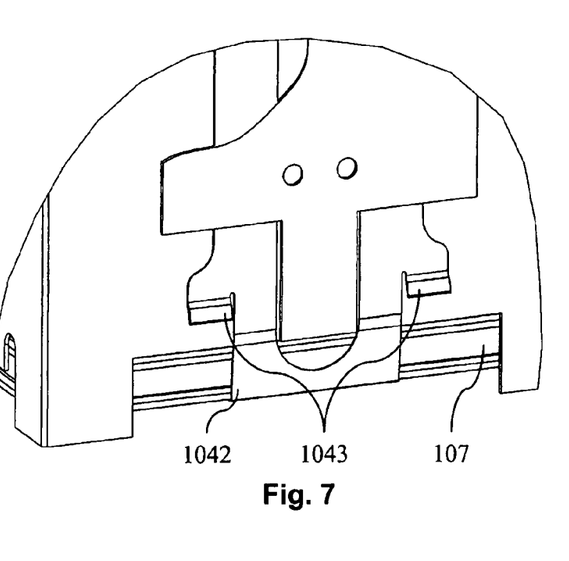
FIG. 7 shows a detailed view of the retaining means of the stacker of FIG. 6 for retaining microplates inside the stacker according to some embodiments.

FIG. 6 shows an embodiment of a stacker 104 for use in the robotic storage system. The stacker 104 comprises side walls 1040 and a top wall 1041. The stacker 104 has no bottom wall, instead there is a bottom opening. Microplates 107 are arranged within the stacker 104 one above the other in a stack, and can be moved into the stacker 104 through the bottom opening. The stacker comprises retaining means in form of resilient clamps 1042 to secure the stack of microplates 107 inside the stacker 104 when they are not actuated. Release clips 1043 are provided in order to actuate and thus to release the resilient clamps 1042 for either moving another microplate into the stacker 104 or for removing one or more microplates 107 from the stacker 104. FIG. 7 shows in detail the resilient clamps 1042 and the release clips 1043 of the stacker 104.

Figure 8:
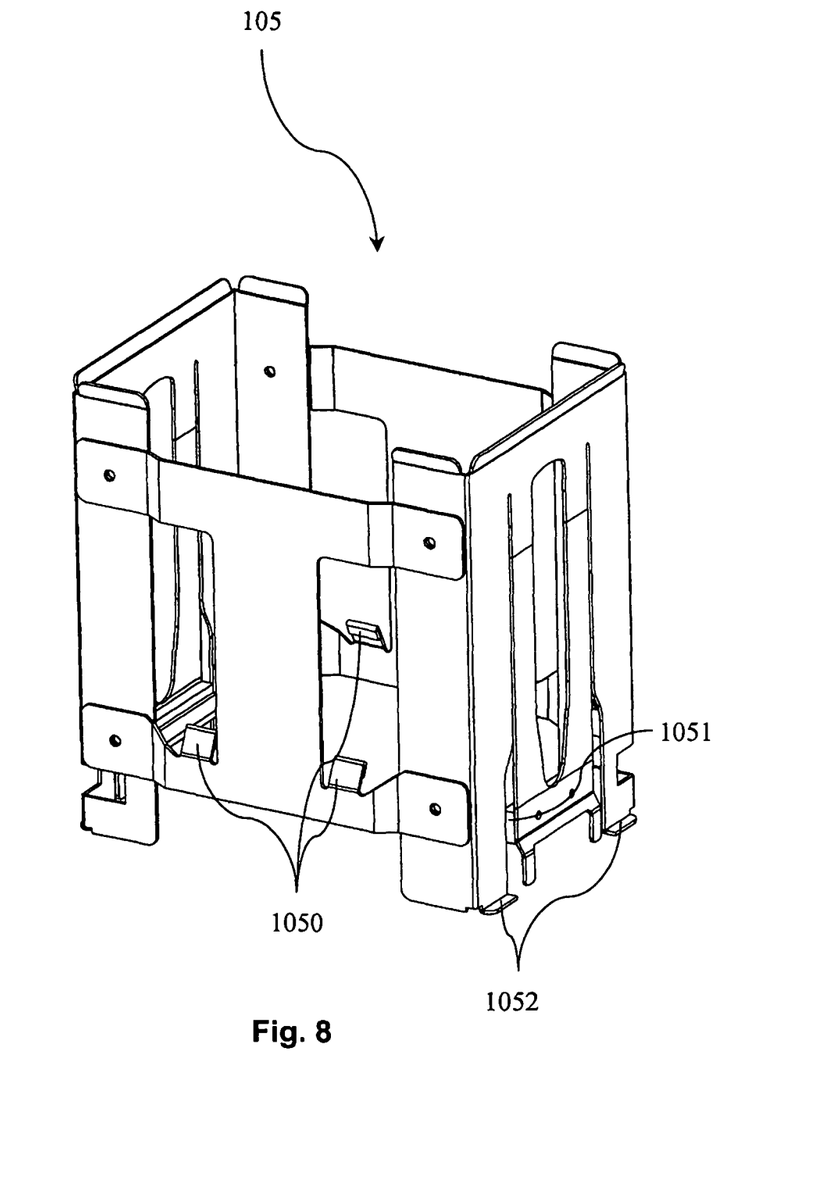
FIG. 8 shows a perspective view of an embodiment of a stacker adapter according to some embodiments.

FIG. 8 shows an embodiment of a stacker adapter 105 according to the invention. The stacker adapter 105 comprises means for matching microplate stackers which are otherwise incompatible with the docking units of the processing station. The stacker adapter 105 comprises first engagement means in form of comparatively stiff latches 1050 for receiving incompatible stackers and second engagement means in form of tongues 1052 for allowing the stacker adapter 105 to be received by the respective docking unit. The comparatively stiff latches 1050 of the stacker adapter 105 actuate the retaining means of the stacker whenever the stacker is inserted in the stacker adapter 105. The stacker adapter 105 further comprises resilient latches 1051 for retaining the released stack of microplates in the stacker whenever they are not actuated by the releasing means (not shown) of the docking unit. Upon being actuated, the resilient latches 1051 release the said stack of microplates from the stacker.

Figure 9:
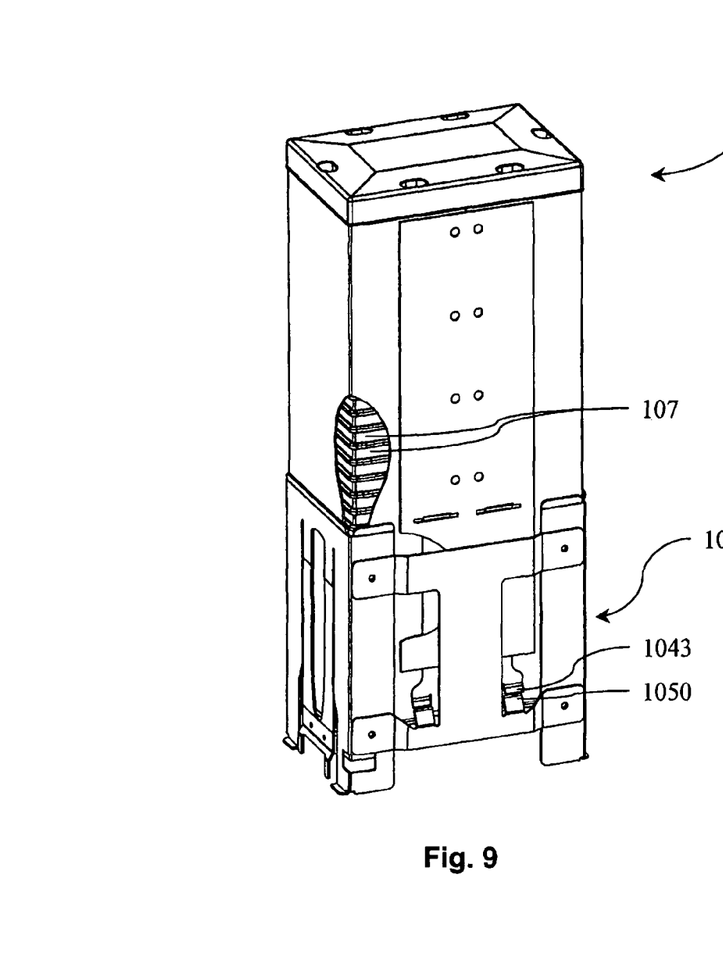
FIG. 9 shows a perspective view of the stacker of FIG. 6 incompletely inserted into the stacker adapter of FIG. 8, according to some embodiments.
Figure 10:
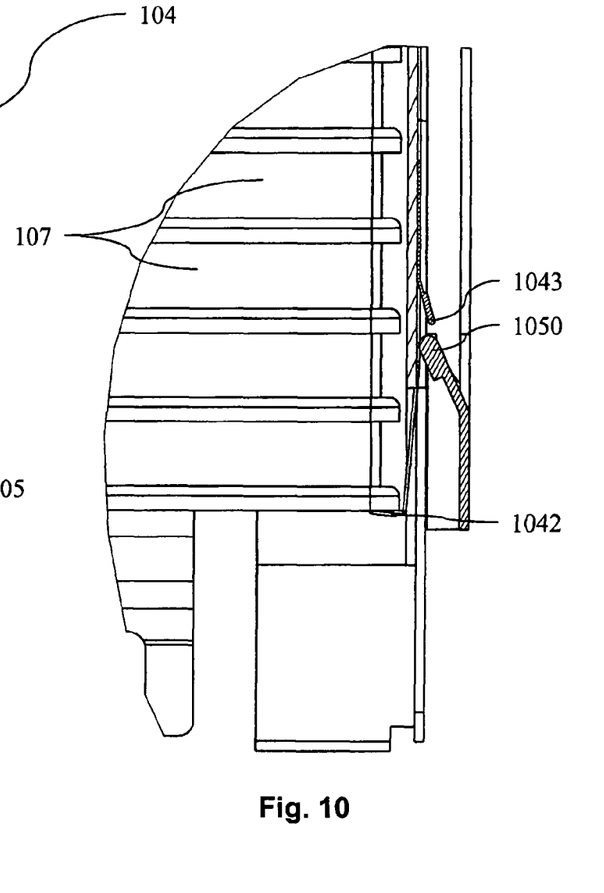
FIG. 10 shows a detailed view of the retaining means of the stacker with the stacker being incompletely inserted into the stacker adapter as in FIG. 9, according to some embodiments.

FIGS. 9 and 10 show a stacker 104 incompletely inserted into the stacker adapter 105. The latches 1050 are not in engagement with the release clips 1043 of the stacker 104. Therefore, the resilient clamps 1042 are still retaining the microplates 107 inside the stacker 104.

Figures 11, 12:
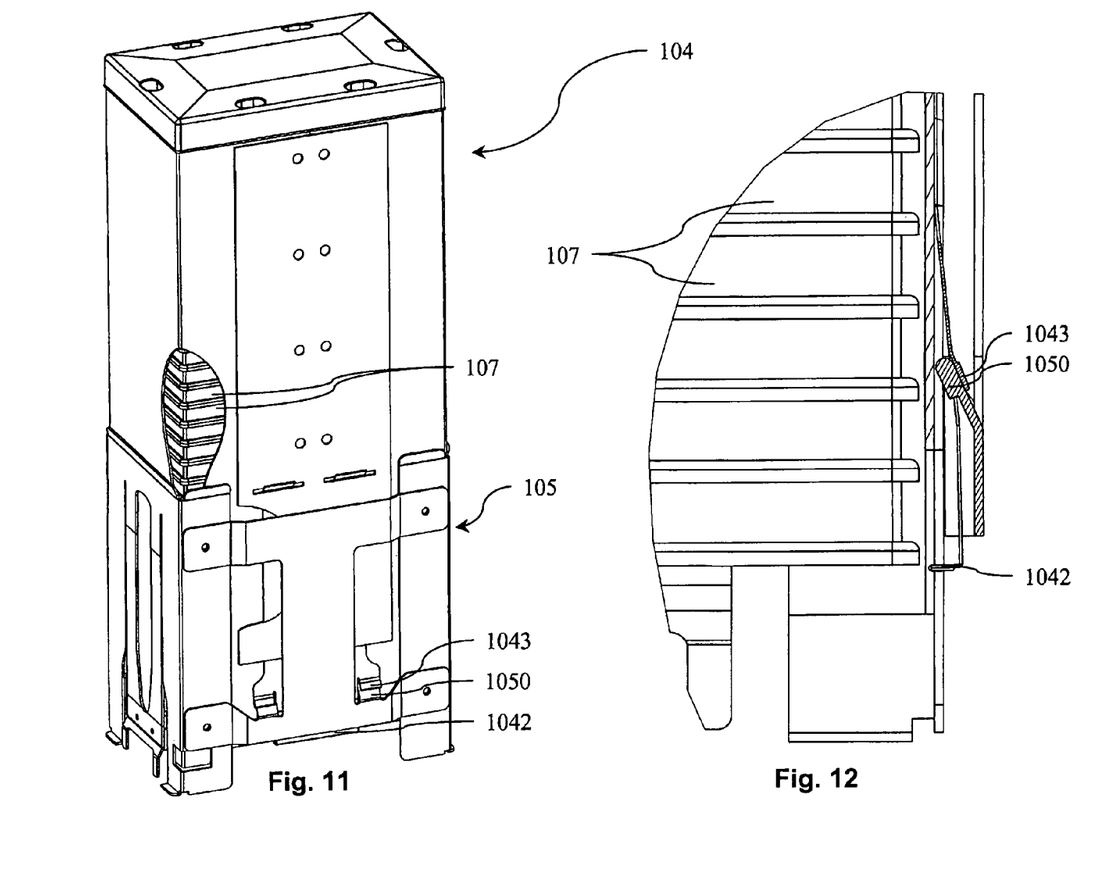
FIG. 11 shows a perspective view of the stacker of FIG. 6 completely inserted into the stacker adapter of FIG. 8.
FIG. 12 shows a detailed view of the retaining means of the stacker with the stacker being completely inserted into the stacker adapter as in FIG. 11, according to some embodiments.

FIGS. 11 and 12 show a stacker 104 completely inserted into a stacker adapter 105. The resilient clamps 1042 and the release clips 1043 of the stacker 104 are fully deflected by the latches 1050. Thus, the resilient clamps 1042 are actuated and the microplates 107 can be removed from the stacker 104.

Figure 13:
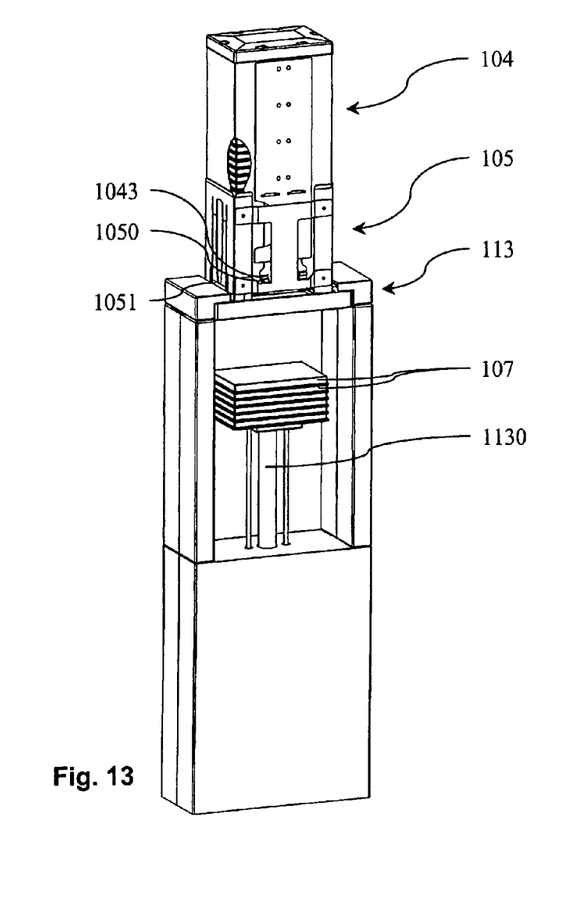
FIG. 13 shows the stacker of FIG. 6 inserted in the stacker adapter of FIG. 8 and placed on a docking unit of the processing station with the docking unit comprising a lift, according to some embodiments.

FIG. 13 shows a stacker 104 fully inserted into a stacker adapter 105. The stacker adapter 105 itself is inserted into a docking unit 113 of a processing station 111 (see FIGS. 1-4). Release clips 1043 of the stacker 104 are fully deflected by the latches 1050. Releasing of the microplates 107 from the stacker is then controlled by the resilient latches 1051 of the stacker adapter 105. The docking unit 113 comprises a lift 1130 capable of moving microplates 107 into and out of the stacker 104. Generally, it is possible to have docking units 113 with a said lift 1130 together with docking units 1130 not having a said lift 1130 on the same processing station.

Figure 14:
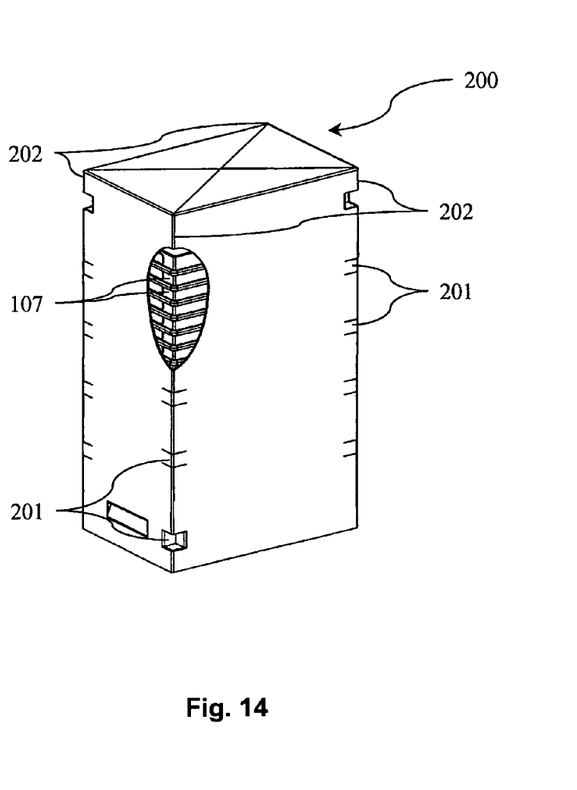
FIG. 14 shows a perspective view of an embodiment of a container, e.g., a cardboard box) according to some embodiments.

FIG. 14 shows an embodiment of a cardboard box 200 according to the invention. The cardboard box 200 comprises deformable sections 201 diagonally oppositely arranged on at least two edges 202 of the cardboard box 200 for securing the microplates 107 arranged one above the other in the cardboard box 200. In the embodiment shown, the deformable sections 201 are pre-perforated in order to easily activate the securing of the microplates 107 arranged one above the other in the cardboard box 200.

What is claimed is:

1. A robotic storage system for storing microplates carrying a plurality of sample tubes, the system comprising:
    a freezer room operated at a temperature of about −20° C., the freezer room having a plurality of freezing units for storing a plurality of microplates arranged in one or more microplate recipients;
    first and second processing rooms operated at a temperature of about −20° C. and arranged at opposite ends of the freezer room, each of the processing rooms comprising a processing station having at least one tube transfer module as well as a transfer robot for moving the microplates between the microplate recipients and the at least one tube transfer module, the at least one tube transfer module being a tube punching module or a tube picking module for transferring a tube from a source microplate to a destination microplate;
    a moving robot movable between the freezer room and the processing rooms to move the microplates therebetween, and to transfer the microplates between the freezing units of the freezer room and the processing stations of the processing rooms; and
    a first thermally insulating door for thermally separating the first processing room from the freezer room, and a second thermally insulating door separate from the first thermally insulating door for thermally separating the second processing room from the freezer room, the first and second thermally insulating door being configured and arranged to allow a continuous operation of the robotic storage system while one of the first and second processing rooms is heated to an elevated temperature above −20° C. for performance of maintenance work in the heated processing room.

2. The robotic storage system of claim 1, wherein the freezer units include a door and a plurality of drawers, and wherein each drawer is designed to store a plurality of microplate recipients.

3. The robotic storage system of claim 1, wherein the moving robot includes means for carrying at least two microplate recipients at a time.

4. The robotic storage system of claim 1, wherein the microplate recipients comprise stackers and/or storage hotels.

5. The robotic storage system of claim 1, wherein the processing station further comprises at least one docking unit for receiving microplate recipients transferred from the moving robot to the processing station and for allowing the moving robot to transfer microplate recipients from the processing station to the freezing units.

6. The robotic storage system of claim 5, wherein the docking units for microplate recipients comprise means for allowing access to each of the microplates arranged in a said stacker and/or in a said storage hotel.

7. The robotic storage system of claim 6, wherein the means for allowing access to each of the microplates arranged in a said stacker comprise releasing means for actuating a retaining means of the stacker, enabling release of the stack of the microplates from the stacker and a lift for lowering the released stack of microplates to the desired microplate.

8. The robotic storage system of claim 6, wherein the storage hotels comprise a cover and wherein the means for allowing access to each of the microplates arranged in a said storage hotel comprise means for removing the cover.

9. The robotic storage system according to claim 1, wherein the at least one processing room comprises an intermediate freezer for intermediate storage of microplate recipients which have been customized in the processing station, and wherein the intermediate freezer is accessible from inside the processing room by the moving robot for moving microplate recipients into the intermediate freezer or for removing microplate recipients from the intermediate freezer, and from outside the processing room by the user for removing microplate recipients from the intermediate freezer or for moving microplate recipients into the intermediate freezer.

10. The robotic storage system of claim 1, wherein the processing station further comprises at least one docking unit for receiving microplate recipients transferred from the moving robot to the processing station and for allowing the moving robot to transfer microplate recipients from the processing station to the freezing units.

11. The robotic storage system of claim 5, wherein the freezer units include a door and a plurality of drawers, and wherein each drawer is designed to store a plurality of microplate recipients.

12. The robotic storage system of claim 5, wherein the microplate recipients comprise stackers and/or storage hotels.

13. The robotic storage system of claim 1, wherein the first and second thermally insulating doors are openable to allow the moving robot to pass therethrough to move between the freezer room and the processing rooms.

14. The robotic storage system of claim 1, wherein the maintenance work is performed by a single person in the heated room.

15. The robotic storage system of claim 1, further comprising a track on which the moving robot travels, the track extending from the first processing room through the freezer room to the second processing room.

* * * * *